(12) United States Patent
Lenchig, Jr.

(10) Patent No.: US 8,434,942 B2
(45) Date of Patent: May 7, 2013

(54) LIGHTING APPARATUS FOR A C-ARM X-RAY MACHINE

(76) Inventor: Sergio Lenchig, Jr., Miami, FL (US)

( * ) Notice: Subject to any disclaimer, the term of this patent is extended or adjusted under 35 U.S.C. 154(b) by 189 days.

(21) Appl. No.: 13/072,506

(22) Filed: Mar. 25, 2011

(65) Prior Publication Data
US 2012/0243666 A1    Sep. 27, 2012

(51) Int. Cl.
*H05G 1/00*    (2006.01)
(52) U.S. Cl.
USPC .......................................... 378/204; 378/206
(58) Field of Classification Search ............. 378/204, 378/206
See application file for complete search history.

(56) References Cited

U.S. PATENT DOCUMENTS 5,661,775 A * 8/1997 Cramer et al. ............... 378/206

* cited by examiner

*Primary Examiner* — Hoon Song
(74) *Attorney, Agent, or Firm* — Mark Terry

(57) ABSTRACT

A lighting apparatus for a C-arm X-ray apparatus is disclosed. The lighting apparatus comprises a housing that surrounds an X-ray receiving element of the X-ray fluoroscope and does not cover a receiving face of the X-ray receiving element. The lighting apparatus further comprises at least one light-emitting element positioned within the housing so as to surround the X-ray receiving element, the at least one light-emitting element being configured for emitting visible light downwards towards an X-ray emitting element of the X-ray fluoroscope. The lighting apparatus further comprises a focusing mechanism that allows for focusing of the light emitted, a fastener for coupling the housing to the X-ray receiving element and a power supply unit for providing an electrical current to the at least one light-emitting element.

14 Claims, 4 Drawing Sheets

LIGHTING APPARATUS FOR A C-ARM X-RAY MACHINE

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of medical lighting, and more particularly relates to the field of lighting for use with C-arm X-ray machines.

BACKGROUND OF THE INVENTION

Various medical procedures and operations in the fields of interventional pain management, orthopedics, interventional radiology, and vascular surgery, among others, require the insertion of a tool or instrument into a patient's body at a predetermined trajectory. A C-arm X-ray fluoroscope 10 (see FIG. 1) is a well-known X-ray apparatus used for just such a procedure, wherein one or more digital X-ray images are produced of the procedural zone. From the generated digital views it is possible to determine the location of some or all of the patient's skeletal and vascular structures, as well as the location of the doctor's or technician's tool or instrument. Using that method, the path of insertion for a tool or instrument can be accurately determined. A conventional C-arm X-ray fluoroscope comprises a C-shaped arm element 12, a base 18 providing a foundation for the C-shaped arm element, an X-ray receiving element 14 located at a top end of the C-shaped arm element and an X-ray emitting element 16 located at a bottom end of the C-shaped arm element. The patient that is the subject of the procedure is located between elements 14 and 16. A conventional C-arm X-ray fluoroscope may also comprise one or more displays 20 for viewing digital X-ray images of the patient generated by the C-arm X-ray fluoroscope 10.

In practice, the actual aiming of the tool or instrument is an inaccurate art, and multiple attempts are usually made, requiring a repositioning of the tool, the drapes and the doctor or technician each time. This can be time-consuming and tedious. This problem is further compounded by the fact that the lights in the operating room often must be turned off in order to better see the displays 20. This is problematic because it reduces the illumination of the patient located between the elements 14 and 16. As such, the doctor or technician cannot adequately see the zone of operation where his hands, the instrument and the patient are located. It is imperative that the zone of operation is adequately illuminated so that the doctor or technician can see what is occurring and be able to act quickly and appropriately, while enhancing patient safety as well as the resolution of the visualized monitors.

Therefore, a need exists to overcome the problems with the prior art as discussed above, and particularly for a solution to the dearth of lighting equipment available for use with C-arm X-ray machines.

SUMMARY OF THE INVENTION

Briefly, according to an embodiment of the present invention, a lighting apparatus for a C-arm X-ray apparatus is disclosed. The lighting apparatus comprises a housing that surrounds an X-ray receiving element of the X-ray fluoroscope and does not cover a receiving face of the X-ray receiving element. The lighting apparatus further comprises at least one light-emitting element positioned within the housing so as to surround the X-ray receiving element, the light-emitting element being configured for emitting visible light towards an X-ray emitting element of the X-ray fluoroscope. The lighting apparatus further comprises a focusing mechanism that allows focusing of the light emitted, a fastener for coupling the housing to the X-ray receiving element and a power supply unit for providing an electrical current to the light emitting element.

In another embodiment of the present invention, a C-arm X-ray apparatus is disclosed. The C-arm X-ray apparatus comprises a C-shaped arm element, a base providing a foundation for the C-shaped arm element, an X-ray receiving element located at a top end of the C-shaped arm element and an X-ray emitting element located at a bottom end of the C-shaped arm element. The C-arm X-ray apparatus further comprises a lighting apparatus including a housing that surrounds the X-ray receiving element of the X-ray apparatus and does not cover a receiving face of the X-ray receiving element. The lighting apparatus further comprises at least one light-emitting element positioned within the housing so as to surround the X-ray receiving element, the light-emitting element being configured for emitting visible light towards the X-ray emitting element of the X-ray apparatus. The lighting apparatus further comprises a focusing mechanism that allows for focusing of the light emitted, a fastener for coupling the housing to the X-ray receiving element and a power supply unit for providing an electrical current to the light emitting element.

The foregoing and other features and advantages of the present invention will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings. Additionally, the left-most digit of a reference number identifies the drawing in which the reference number first appears.

DETAILED DESCRIPTION

The present invention solves problems with the prior art by providing a simple and easy-to-use lighting device that can be used in conjunction with a C-arm X-ray fluoroscope. The apparatus of the present invention provides a mechanism that illuminates the zone of operation for a doctor or technician, without obstructing or impeding the functionality of the C-arm X-ray fluoroscope. The Applicant's invention further provides a lighting apparatus that allows the doctor or technician to turn off the ambient light in an operating room—so as to better view the X-ray displays—while still providing illumination of the operative zone so that the doctor may see what is occurring and be able to act quickly and appropriately.

Furthermore, the present invention does not require readjustment of the lighting apparatus if the C-arm is moved, since the lighting apparatus is attached to the X-ray receiving element of the X-ray fluoroscope and the X-ray receiving element is always pointed at the zone of operation. Thus, if adjustments must be made to the C-arm position by the surgeon, the lighting apparatus will still be pointed at the proper location at the patient and need not be adjusted. This results in less work for the surgeon and faster operation times. Finally, the present invention is advantageous since it allows an operator to quickly and easily adjust the light emitted by the lighting apparatus by providing controls for focusing or beam condensing the light, changing the color of the light, dimming the light and adjusting the amplitude or intensity of the light.

Figure 1:
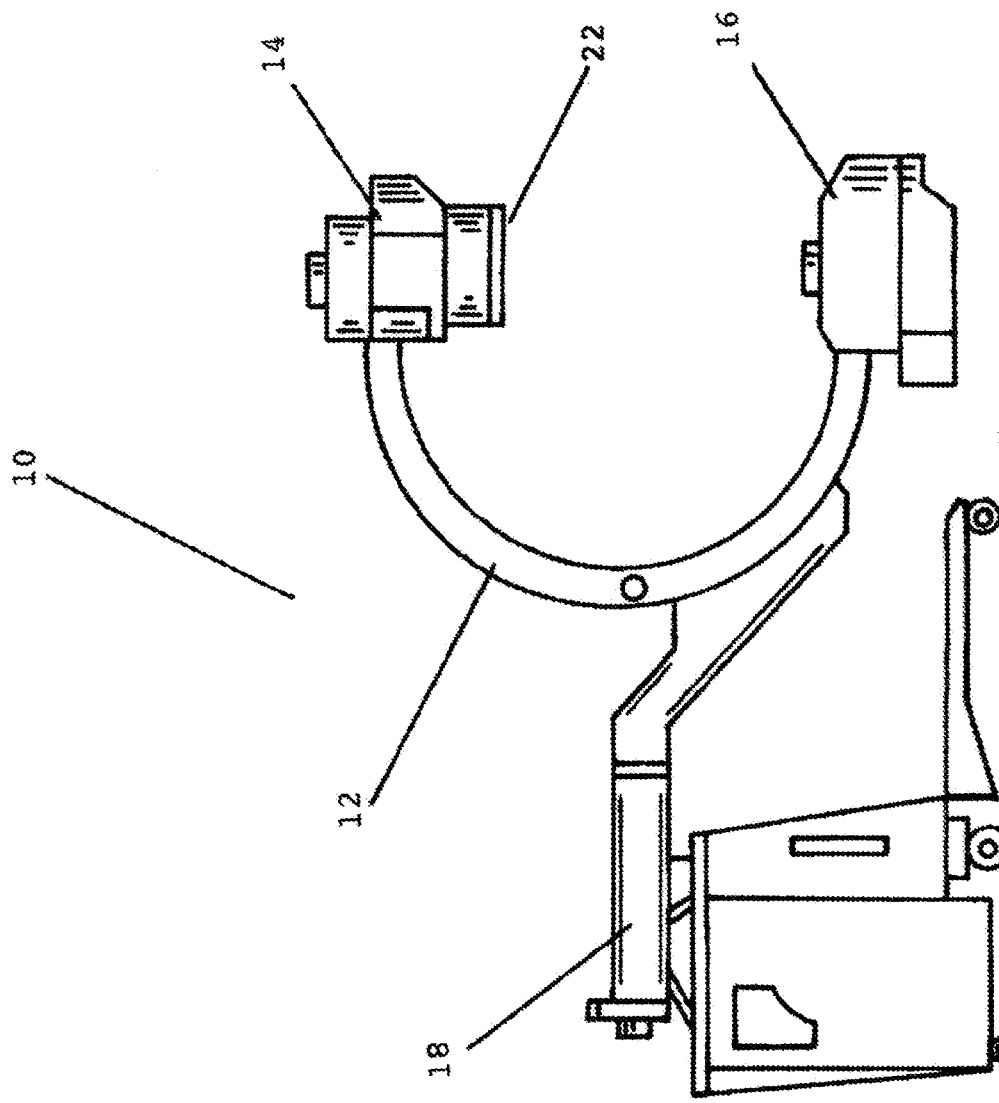
FIG. 1 is an illustration of a side view of a C-arm X-ray fluoroscope, which is well known in the art.
Figure 1:
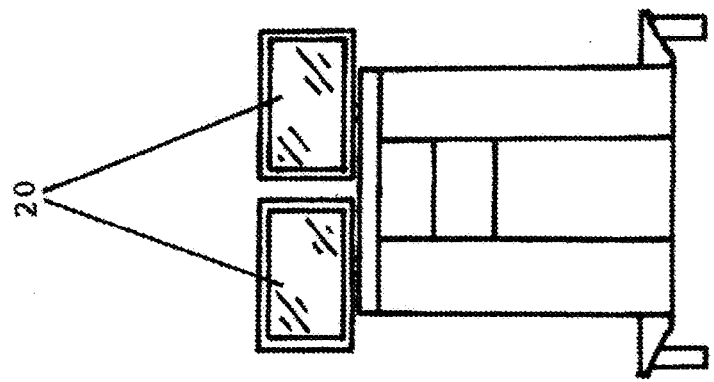

FIG. 1 is an illustration of a side view of a C-arm X-ray fluoroscope 10, which is well known in the art. The C-arm X-ray fluoroscope comprises a C-shaped arm element 12, a base 18 providing a foundation for the C-shaped arm element, an X-ray receiving element 14 located at a top end of the C-shaped arm element and an X-ray emitting element 16 located at a bottom end of the C-shaped arm element. Note the bottom-facing surface 22 of the X-ray receiving element 14. FIG. 1 also shows one or more displays 20 for viewing digital X-ray images of the patient generated by the C-arm X-ray fluoroscope 10.

Figure 2:
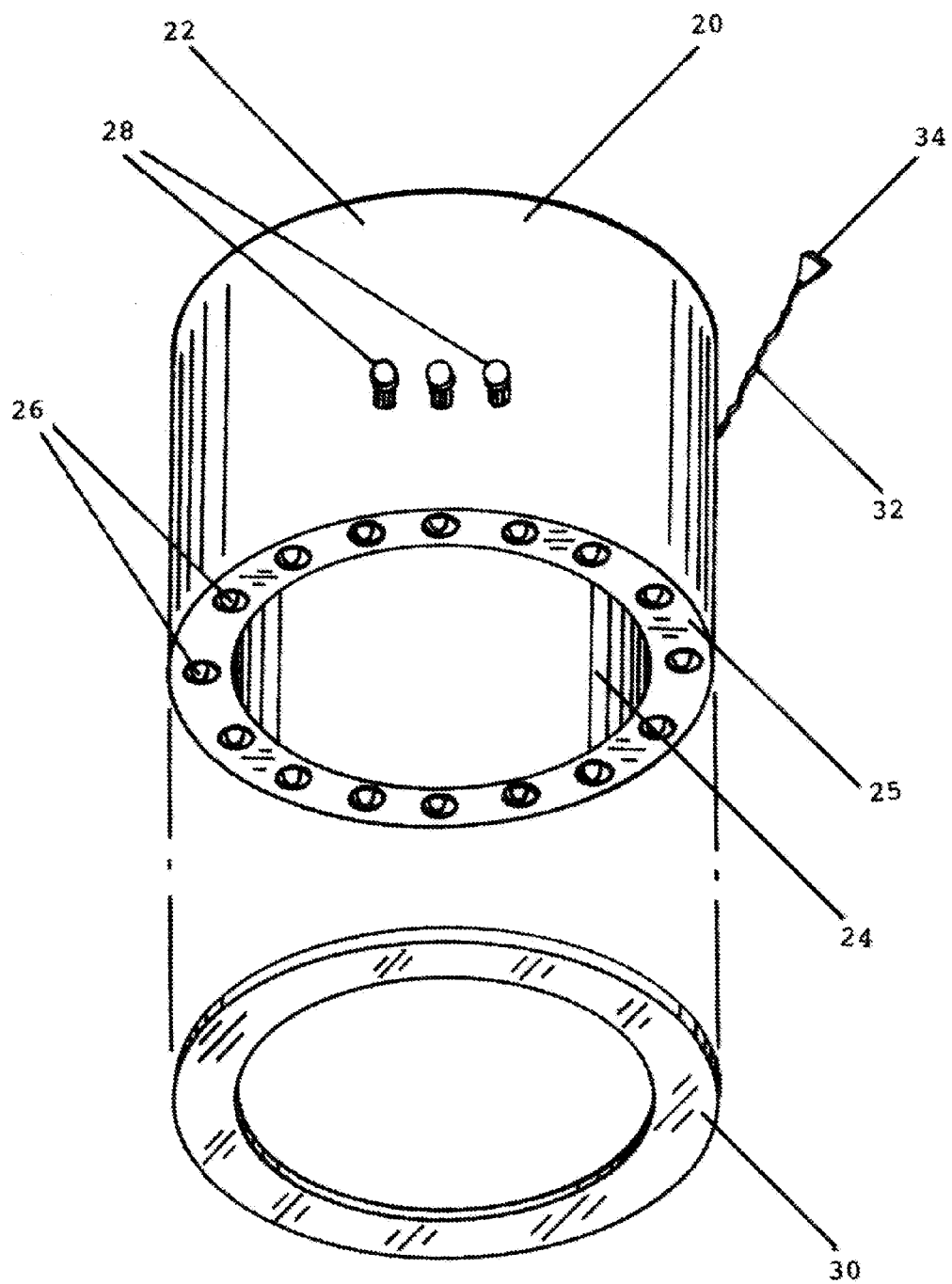
FIG. 2 is a perspective view of the lighting apparatus for a C-arm X-ray fluoroscope, in accordance with one embodiment of the present invention.

FIG. 2 is a perspective view of the lighting apparatus 20 for a C-arm X-ray fluoroscope 10, in accordance with one embodiment of the present invention. Lighting apparatus 20 is composed of a housing 22 which comprises a shell having a cylindrical shape with a hollow interior providing the orifice 24 that extends through the cylinder of apparatus 20. Note there is a thickness to the surface of the cylinder shape. In other embodiments, the lighting apparatus 20 is any shape with a fixed cross-sectional profile and a hollow interior, such as a cuboid shape, a cubic shape, or a prism shape. The fixed cross-sectional profile may be triangular, rectangular, elliptical, circular or any polygonal shape.

Figure 3:
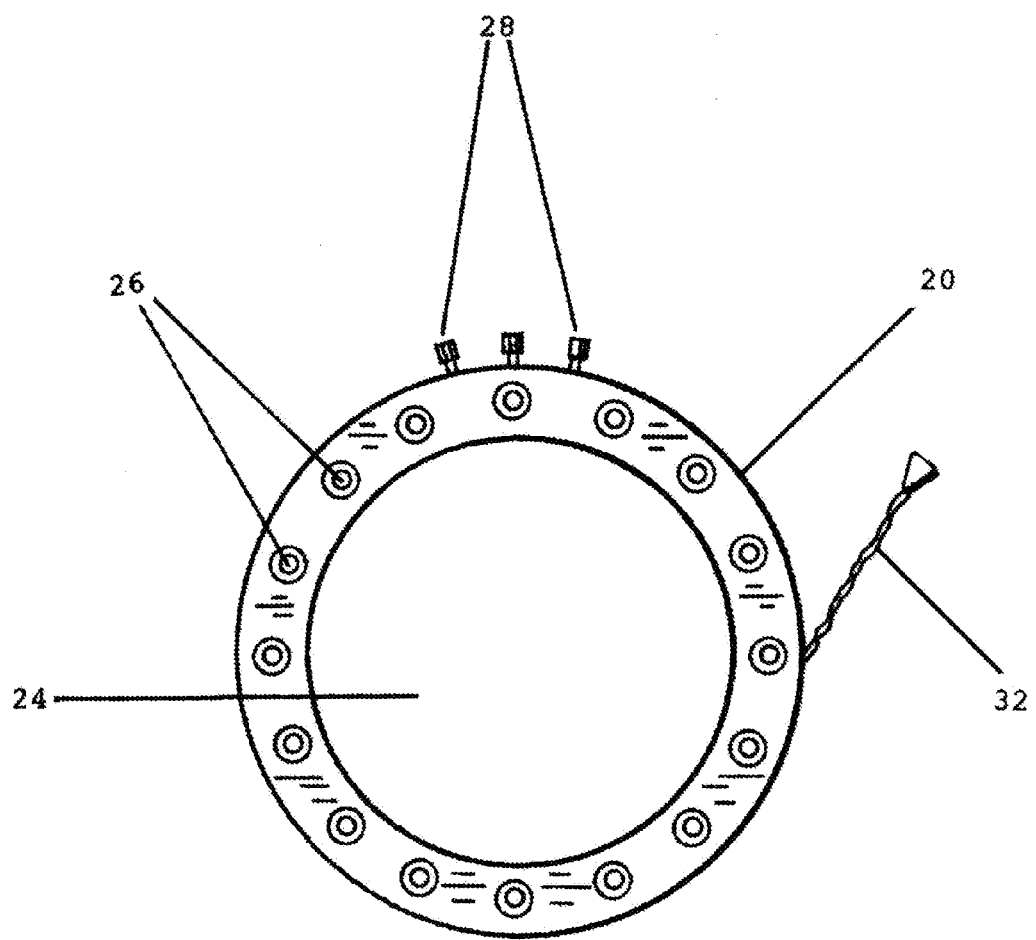
FIG. 3 is a bottom view of the lighting apparatus for a C-arm X-ray fluoroscope, in accordance with one embodiment of the present invention.

FIG. 2 shows that lighting apparatus 20 includes a downwards-facing plane 25, wherein one or more light-emitting elements 26 is positioned around the downwards-facing plane 25. The one or more light-emitting elements 26 may be positioned evenly around the downwards-facing plane 25. Preferably, the light-emitting elements 26 may comprise light emitting diodes (LEDs) but may also comprise all the other well-known light emitting elements, such as, but not limited to, fluorescent bulbs, incandescent and gas filled. FIG. 3 is a bottom view of the lighting apparatus for a C-arm X-ray fluoroscope, wherein the downward-facing nature of the LEDs 26 are shown.

FIG. 2 also shows an optical element 30 placed over the downwards-facing plane 25 such that the light emitted by the light-emitting elements 26 travels through the optical element 30. Optical element 30 may include refractive materials such as an extruded refractive material. An exemplary material for optical element 30 may be an acrylic material, due to its excellent light transmission and UV light stability properties. An example of a suitable refractive material for optical element 30 is polymethyl methacrylate (PMMA). However, any refractive material with increased light transmission efficiencies and/or UV light stability properties may be used for optical element 30 in accordance with the present invention. Further, optical material with various translucent qualities can be used for optical element 30.

Optical elements 30 may include one or more optical elements that each may include refractive materials such as an extruded refractive material. The type of refractive material may differ in each of optical elements 30. In other words, one of element 30 may comprise a different extruded refractive material than another of element 30. However, one or more of elements 30 may include the same refractive material. An exemplary material for one or more of elements 30 may be an acrylic material, due to its excellent light transmission and UV light stability properties. An example of a suitable refractive material for elements 30 is polymethyl methacrylate. However, any refractive material with increased light transmission efficiencies and/or UV light stability properties may be used for elements 30 in accordance with the present invention. Further, optical material with various translucent qualities can be used for one or more elements 30.

In operation, elements 30 act together to refract light emanating from one or more single point light sources (the LEDs 26) and thereby increase the light-transmission efficiency of apparatus 20. As an LED produces light, the light enters a first of element 30, which harnesses the light and refracts it so as to direct the light into another of element 30. For example, a first of element 30 may collimate light emitted from the LEDs 20. A second of element 30 may allow for total internal reflection of the light entering it, for example. Once light produced by LEDs has been received by the first of element 30 and refracted towards a second of element 30, the second of element 30 then refracts the light again to direct the light in a desired direction. For example, the second of element 30 may be customized to direct light in a 45 degree beam pattern, or spread.

One or more of elements 30 may also provide for inter-reflectance of light emitted by the LEDs 26 so as to mix colors of light emitted by various LEDs. For example, elements 30 may be used to mix different colored light emitted by two or more LEDs or to mix similarly colored light emitted by two or more LEDs to provide a more uniform light emitted by element 30. In addition, one or more of elements 30 may operate alone or together to refract light emitted from the LEDs 26 into a continuous light beam. For example, each LED may provide a single point of light. One or more of elements 30 may refract light from one or more LEDs so as to cause light emitted by element 30 to be continuous and approximately uniform as it emanates from element 30.

The combination of elements 30 provide for an efficient lighting apparatus 20. As described above, element 30 harnesses light emitted by LEDs 26 so that the amount of light entering element 30 is maximized. Element 30 may then be used to direct, diffuse or refract light in any one of a number of customizable and desired ways. In this way, elements 30 act in series to refract light from LEDs 26.

The lighting apparatus 20 further includes a focusing or beam condensing mechanism comprising a mechanism for moving the optical element(s) 30 so as to adjust the focus of the light emitted by LEDs 26 and/or to condense its beams. To this end, the lighting apparatus 20 further includes one or more knobs 28 for use by an operator in engaging the focusing or beam condensing mechanism for moving the optical element 30 so as to adjust the focus of the light emitted and/or to condense its beams. In one embodiment, the one or more knobs 28 can also be used by an operator to change the color temperature of the light emitted by LEDs 26, to dim the light, to change the amplitude or intensity of the light. In another embodiment, the one or more knobs 28 can also be used by an operator to change the angle at which each of the LEDs 26 emits light. That is, the direction in which each LED points may be adjusted so as to focus the light, or condense the beams, of all LEDs in one place, or disperse the light. Note also that although FIG. 2 shows knobs 28 for controlling various aspects of apparatus 20, a remote control may be used to control the same aspects of apparatus 20. In one embodiment, the knobs 28 may be located in the main frame of the apparatus 10 to be operated by an assistant or in the X-ray receiving element 14 to be operated by the surgeon, in which case disposable caps may be placed over the knobs to cover them and be managed without compromising the sterile condition of the operator.

The lighting apparatus 20 may further include a conductive element 32 coupled to the power supply unit of the apparatus 20. Conductive element 32 is positioned on an exterior of the housing 22 and couples with a power source for providing the electrical current necessary to power the power supply unit, which in turn powers the one or more light emitting elements 26. To this end, the lighting apparatus 20 may further include an electronic interconnect 34 coupled to an end of the conductive element 32 for coupling with a terminal providing access to the power source.

Figure 4:
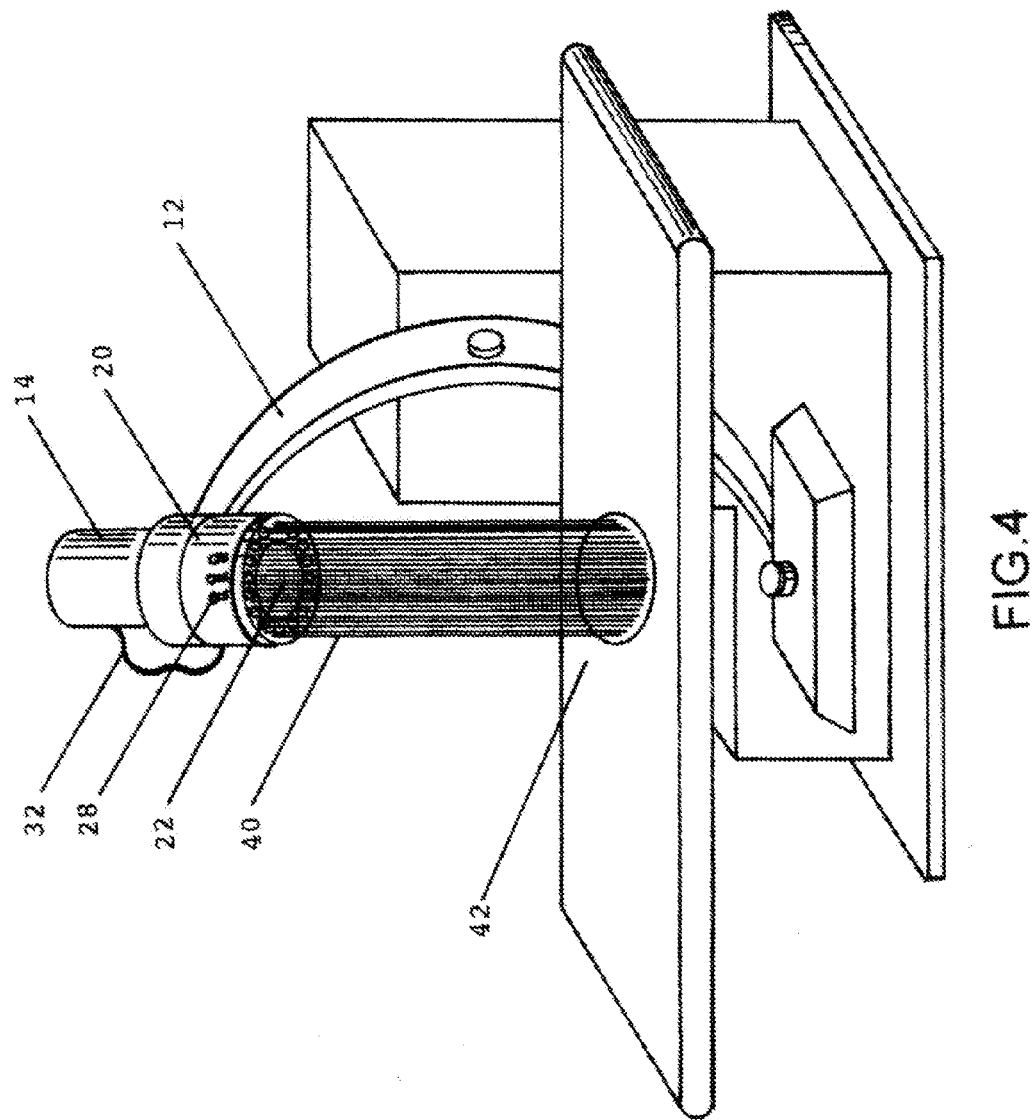
FIG. 4 is a perspective view of the lighting apparatus shown in an assembled state with a C-arm X-ray fluoroscope, in accordance with one embodiment of the present invention.

FIG. 4 is a perspective view of the lighting apparatus 20 shown in an assembled state with a C-arm X-ray fluoroscope 10, in accordance with one embodiment of the present invention. FIG. 4 shows that the housing 22 fits around the X-ray element 14 so as to surround it but still allowing the bottom-facing surface 22 of the X-ray receiving element 14 to be exposed. This arrangement allows the X-ray apparatus 10 to operate normally without any obstructions or obtrusions. FIG. 4 also shows that electronic interconnect 34, coupled to an end of the conductive element 32, has been coupled with a terminal of the X-ray apparatus 10, which terminal provides access to a power source.

FIG. 4 further shows that lighting apparatus 20 shines a light canopy 40 downwards towards the X-ray emitting element 16 of the X-ray fluoroscope 10. The light canopy 40 is focused on plane 42, which represents the location of the patient being operated upon. One or more knobs 28 may be used by an operator in engaging the focusing or beam condensing mechanism for moving the optical element 30 so as to adjust the focus of the light canopy 40 emitted or condense its beams. Note that although this disclosure discusses an embodiment wherein the lighting apparatus 20 is an object separate and distinct from the X-ray fluoroscope 10 and is attached to the X-ray fluoroscope 10 by a user or technician, the present invention also supports an implantation wherein the lighting apparatus 20 is integrally formed with, or is an integral part of, the X-ray fluoroscope 10.

Note that FIG. 4 shows that the housing 22 fits around the X-ray element 14 so as to surround it. The housing 20 may be fastened to the X-ray element 14 using a fastener such as a bolt. In another embodiment, the housing 22 includes a protrusion located within the hollow interior of the housing 22, wherein the protrusion produces a friction fit between the housing 22 and the X-ray receiving element 14. The protrusion may comprise a circular bump or bulge that extends around a circumference of the interior surface of the housing 22.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

The invention claimed is:

1. A lighting apparatus for a C-arm X-ray apparatus, comprising:
    (a) a housing that surrounds an X-ray receiving element of the X-ray fluoroscope and does not cover a receiving face of the X-ray receiving element;
    (b) a plurality of light emitting diodes (LEDs) distributed evenly around a circumference of a downwards facing end of the housing, wherein the plurality of LEDs are positioned within the housing so as to surround the X-ray receiving element;
    (c) the plurality of LEDs being configured for emitting visible light towards an X-ray emitting element of the X-ray fluoroscope;
    (d) a first optical element placed over the downwards-facing end of the housing such that the light emitted by the plurality of LEDs travels through the first optical element, and wherein the first optical element refracts the light travelling through the first optical element;
    (e) a second optical element placed over the first optical element such that the light that has travelled through the first optical element subsequently travels through the second optical element, and wherein the second optical element diffuses the light travelling through the first optical element;
    (f) a focusing mechanism that allows for focusing of the light emitted;
    (g) a fastener for coupling the housing to the X-ray receiving element; and
    (h) a power supply unit for providing an electrical current to the at least one light-emitting element.

2. The lighting apparatus of claim 1, wherein the housing comprises a fixed cross-sectional profile.

3. The lighting apparatus of claim 2, wherein the housing comprises a cylindrical shape with a hollow interior.

4. The lighting apparatus of claim 2, wherein the plurality of LEDs are positioned around a brim of the downwards-facing end of the housing.

5. The lighting apparatus of claim 4, further comprising a third optical element placed over the second optical element such that the light that has travelled through the second optical element subsequently travels through the third optical element.

6. The lighting apparatus of claim 5, wherein the focusing mechanism comprises a mechanism for moving the first, second and/or third optical elements so as to adjust the focus of the light emitted.

7. The lighting apparatus of claim 6, further comprising a knob for use by an operator in engaging the focusing mechanism for moving the first, second and/or third optical elements so as to adjust the focus of the light emitted.

8. The lighting apparatus of claim 2, wherein the fastener for coupling the housing to the X-ray receiving element comprises at least one bolt.

9. The lighting apparatus of claim 2, further comprising a conductive element coupled with the power supply unit, the conductive element positioned on an exterior of the housing and for coupling to an external power source.

10. The lighting apparatus of claim 9, further comprising an electronic interconnect coupled to an end of the conductive element and for connecting with a terminal for an external power source.

11. A C-arm X-ray apparatus, comprising:
a C-shaped arm element;
a base providing a foundation for the C-shaped arm element;
an X-ray receiving element located at a top end of the C-shaped arm element;
an X-ray emitting element located at a bottom end of the C-shaped arm element; and
a lighting apparatus comprising:
 (a) a housing that surrounds the X-ray receiving element of the X-ray apparatus and does not cover a receiving face of the X-ray receiving element;
 (b) a plurality of light emitting diodes (LEDs) distributed evenly around a circumference of a downwards facing end of the housing, wherein the plurality of LEDs are positioned within the housing so as to surround the X-ray receiving element;
 (c) the plurality of LEDs being configured for emitting visible light towards the X-ray emitting element of the X-ray apparatus;
 (d) a first optical element placed over the downwards-facing end of the housing such that the light emitted by the plurality of LEDs travels through the first optical element, and wherein the first optical element refracts the light travelling through the first optical element;
 (e) a second optical element placed over the first optical element such that the light that has travelled through the first optical element subsequently travels through the second optical element, and wherein the second optical element diffuses the light travelling through the first optical element;
 (f) a focusing mechanism that allows for focusing of the light emitted; and
 (g) a power supply unit for providing an electrical current to the at least one light-emitting element.

12. The C-arm X-ray apparatus of claim 11, wherein the housing comprises a fixed cross-sectional profile.

13. The C-arm X-ray apparatus of claim 12, further comprising a third optical element placed over the second optical element such that the light that has travelled through the second optical element subsequently travels through the third optical element.

14. The C-arm X-ray apparatus of claim 13, wherein the focusing mechanism comprises a mechanism for moving the first, second and/or third optical elements so as to adjust the focus of the light emitted.

* * * * *